US00PP27072P2

(12) United States Plant Patent
Hartman

(10) Patent No.: US PP27,072 P2
(45) Date of Patent: Aug. 16, 2016

(54) ***CALADIUM* PLANT NAMED 'SNOW DRIFT'**

(50) Latin Name: *Caladium×hortulanum*
Varietal Denomination: Snow Drift

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 89 days.

(21) Appl. No.: 14/544,171

(22) Filed: Dec. 4, 2014

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — June Hwu
(74) *Attorney, Agent, or Firm* — C. A. Whealy

(57) ABSTRACT

A new and distinct cultivar of *Caladium* plant named 'Snow Drift', characterized by its intermediate height; compact, upright and uniform plant habit; vigorous growth habit and rapid growth rate; fancy-type leaves that are white in color with green-colored venation and margins; and good landscape performance.

4 Drawing Sheets

Botanical designation: *Caladium×hortulanum.*
Cultivar denomination: 'SNOW DRIFT'.

BACKGROUND OF THE INVENTION

The present invention relates to a new and distinct cultivar of *Caladium* plant, botanically known as *Caladium×hortulanum*, commercially referred to as a fancy leaf-type *Caladium* and hereinafter referred to by the name 'Snow Drift'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2007 in Avon Park, Fla. of *Caladium×hortulanum* 'Victoria', disclosed in U.S. Plant Pat. No. 18,087, as the female, or seed, parent with *Caladium×hortulanum* 'White Christmas', not patented, as the male, or pollen, parent. The new *Caladium* plant was discovered and selected by the Inventor as a single plant within the progeny of the stated cross-pollination in a controlled outdoor nursery environment in Zolfo Springs, Fla. in September, 2008.

Asexual reproduction of the new *Caladium* plant by 'chipping' the tubers (cutting the tuber into segments with each segment containing an axillary bud and tuber cortical tissue) in a controlled outdoor nursery environment in Zolfo Springs, Fla. since April, 2009 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Snow Drift'. These characteristics in combination distinguish 'Snow Drift' as a new and distinct *Caladium* plant:

1. Intermediate in height; compact, upright and uniform plant habit.
2. Vigorous growth habit and rapid growth rate.
3. Fancy-type leaves that are white in color with green-colored venation and margins.
4. Good landscape performance.

Plants of the new *Caladium* differ primarily from plants of the female parent, 'Victoria', in the following characteristics:

1. Plants of the new *Caladium* are taller and more upright than plants of 'Victoria'.
2. Plants of the new *Caladium* are faster growing and produce finished plants about three weeks earlier than plants of 'Victoria'.
3. Plants of the new *Caladium* and 'Victoria' differ in leaf shape and color as leaves of plants of 'Victoria' are lance-types and pink in color with green-colored margins and white-colored borders.
4. Plants of the *Caladium* and 'Victoria' differ in leaf petiole coloration as leaf petioles of plants of 'Victoria' are tan pink to tan pink in color with greenish black-colored streaking and mottling.

Plants of the new *Caladium* differ primarily from plants of the male parent, 'White Christmas', in the following characteristics:

1. Plants of the new *Caladium* are more freely clumping and denser than plants of 'White Christmas'.
2. Plants of the new *Caladium* and 'White Christmas' differ in leaf color as leaves of plants of 'White Christmas' have green-colored interveinal areas.

Plants of the new *Caladium* can be compared to plants of *Caladium×hortulanum* 'Candidum', not patented. In side-by-side comparisons, plants of the new *Caladium* differed primarily from plants of 'Candidum' in the following characteristics:

1. Plants of the new *Caladium* were more compact than plants of 'Candidum'.

2. Plants of the new *Caladium* were more freely clumping and denser than plants of 'Candidum'.
3. Leaves of plants of the new *Caladium* were undulate whereas leaves of plants of 'Candidum' were mostly flat.
4. Plants of the new *Caladium* and 'Candidum' differed in leaf size and color as leaves of plants of 'Candidum' were larger and had darker green-colored venation and margins than leaves of plants of the new *Caladium*.

Plants of the new *Caladium* can also be compared to plants of *Caladium×hortulanum* 'Candidum Senior', not patented. In side-by-side comparisons, plants of the new *Caladium* differed primarily from plants of 'Candidum Senior' in the following characteristics:

1. Plants of the new *Caladium* were more compact than plants of 'Candidum Senior'.
2. Plants of the new *Caladium* were more freely clumping and denser than plants of 'Candidum Senior'.
3. Leaves of plants of the new *Caladium* were undulate whereas leaves of plants of 'Candidum Senior' were mostly flat.
4. Plants of the new *Caladium* and 'Candidum Senior' differed in leaf size and color as leaves of plants of 'Candidum Senior' were larger and were creamy white in color with green-colored venation.
5. Plants of the new *Caladium* and 'Candidum Senior' differed in leaf petiole color as plants of 'Candidum Senior' had almost black or tan green-colored leaf petioles with dark stipes and stippling.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Snow Drift' in a container and grown in a shadehouse (tuber de-eyed).

The photograph at the top of the second sheet is a comparison view of typical potted plants of the female parent, 'Victoria' (left), 'Snow Drift' (center) and the male parent, 'White Christmas' (right).

The photograph at the bottom of the second sheet is a comparison view of typical potted plants of 'Candidum' (left), 'Snow Drift' (center) and 'Candidum Senior' (right).

The photograph at the top of the third sheet is a comparison view of typical plants of 'Snow Drift' grown in containers; the plant on the right has not had its tuber de-eyed and the plant on the left has had its tuber de-eyed prior to planting.

The photograph at the bottom of the third sheet is a close-up view of typical freshly-harvested tubers and roots of 'Snow Drift' plants.

The photograph on the fourth sheet is a side perspective view of typical plants of 'Snow Drift' grown in an open field.

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from about 10,000 to 12,000 foot-candles. Plants grown in the shadehouse were eight weeks old, and plants grown in the outdoor nursery were eight months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Snow Drift'.

Parentage:

*Female, or seed, parent.*—*Caladium×hortulanum* 'Victoria', disclosed in U.S. Plant Pat. No. 18,087.

*Male, or pollen, parent.*—*Caladium×hortulanum* 'White Christmas', not patented.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented and somewhat flattened; individual segments ovate to irregular in shape. Height: About 2.8 cm to 3 cm. Diameter: About 2.2 cm to 5.5 cm. Segment height: About 1.3 cm to 2.2 cm. Segment diameter: About 1.6 cm to 2.2 cm. Texture: Thick, starchy; somewhat brittle. Color: Epidermis, freshly-harvested: Close to 199C to 199D. Epidermis, dried: Close to 200A. Cortical tissue: Close to 11B to 11C. Axillary buds: Close to N170D. Root description: Thick, fleshy contractile roots; color, close to 155C; proximally, faintly tinged with close to 182B to 182C. Rooting habit: Dense.

Plant description:

*Plant type.*—Herbaceous perennial; suitable as a potted plant in containers 15-cm to 25-cm and suitable as a landscape plant in shaded areas.

*Plant and growth habit.*—Intermediate in height; compact, upright and uniformly mounded plant habit; vigorous and dense growth habit; rapid growth rate, potted plants in finished or saleable form in about eight weeks after planting tubers; leaf petioles and leaves arise from one or more growing points on tubers; petioles mostly upright and leaning somewhat outwardly with development.

*Plant height, from soil level to top of foliar plane, shadehouse-grown potted plants.*—About 28 cm to 36 cm.

*Plant diameter or spread, shadehouse-grown potted plants.*—About 32 cm to 38 cm.

*Number of shoots per plant, shadehouse-grown potted plants, tubers not de-eyed.*—About four develop per #1 tuber.

*Number of shoots per plant, shadehouse-grown potted plants, tubers de-eyed.*—About five to six develop per #1 tuber.

*Cataphylls, shadehouse-grown potted plants*.—Length: About 7 cm. Width: About 1 cm. Shape: Lance-shaped. Apex: Acute. Base: Sheathing the stem. Color, inner surface: Close to N155C; colors and patterns of the outside surface are visible on the inner surface. Color, outer surface: Close to 155C and 196D streaked and stippled with close to 199A tinged with close to 147D; with development, color becoming closer to 199A tinged with close to 187B to 187C.

Leaf description:

*Arrangement and type*.—Alternate; simple; fancy-type.

*Length, shadehouse-grown potted plants*.—About 16 cm to 22 cm.

*Width, shadehouse-grown potted plants, flattened*.—About 10.5 cm to 15.5 cm.

*Shape*.—Ovate.

*Apex*.—Acute to acuminate.

*Base*.—Sagittate to peltate.

*Margin*.—Entire; textured and wavy with broad undulations.

*Texture, upper and lower surfaces*.—Smooth, glabrous.

*Luster, upper surface*.—Dull sheen.

*Luster, lower surface*.—Glaucous.

*Venation pattern*.—Pinnate.

*Color, shadehouse-grown potted plants*.—Developing leaves, upper surface: Main color: More white than close to 155C. Margins: Close to 147A. Basal notch: Close to 187B to 187C. Midrib and primary venation: Close to 147A. Lateral venation: Close to 147B. Developing leaves, lower surface: Main color: Close to 155C. Margins: Close to 147B. Basal notch: Close to 187B to 187C. Midrib: Close to 148C to 148D. Primary venation: Close to 147B. Lateral venation: Close to 147B to 147C. Fully expanded leaves, upper surface: Main color: Close to 155C and to more white than close to 155C. Margins: Close to 147A. Basal notch: Close to 187B to 187C; central descending line, close to 185C. Midrib and primary venation: Close to 147A. Lateral venation: Close to 147B and 145D. Fully expanded leaves, lower surface: Main color: Close to 155A. Margins: Close to 187B. Basal notch: Close to 187B to 187C. Midrib: Close to 148D; proximally tinged with close to 199A. Primary venation: Close to 147B. Lateral venation: Close to 147B to 147C.

*Petioles*.—Aspect: Initially upright and straight; with development, leaning somewhat outwardly; flexible. Length, shadehouse-grown potted plants: About 18 cm to 28 cm. Diameter, distal, shadehouse-grown potted plants: About 3.5 mm to 4 mm. Diameter, proximal, shadehouse-grown potted plants: About 5 mm to 9 mm. Texture: Smooth, glabrous; glaucous. Color, shadehouse-grown potted plants, Just below the leaf and petiole junction: Close to 147D or 146D variably tinged, streaked and striped with close to 200B to 200C. Overall: Close to N186A and 200A striped with close to N155B and N170D and tinged with close to 147D. Wing length, shadehouse-grown potted plants: About 3 cm to 5 cm. Wing diameter, shadehouse-grown potted plants: About 5 mm to 9 mm. Texture, inner and outer surfaces: Smooth, glabrous. Wing color, shadehouse-grown potted plants, inner surface: Close to N155C. Wing color, shadehouse-grown potted plants, outer surface: Close to 155C and 196D, streaked, stippled and striped with close to 199A and tinged with close to 147D.

Inflorescence description: To date, inflorescence development has not been observed on shadehouse-grown potted plants nor on outdoor nursery-grown plants.

Disease & pest tolerance: Plants of the new *Caladium* have been observed to have above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11.

It is claimed:

1. A new and distinct *Caladium* plant named 'Snow Drift' as illustrated and described.

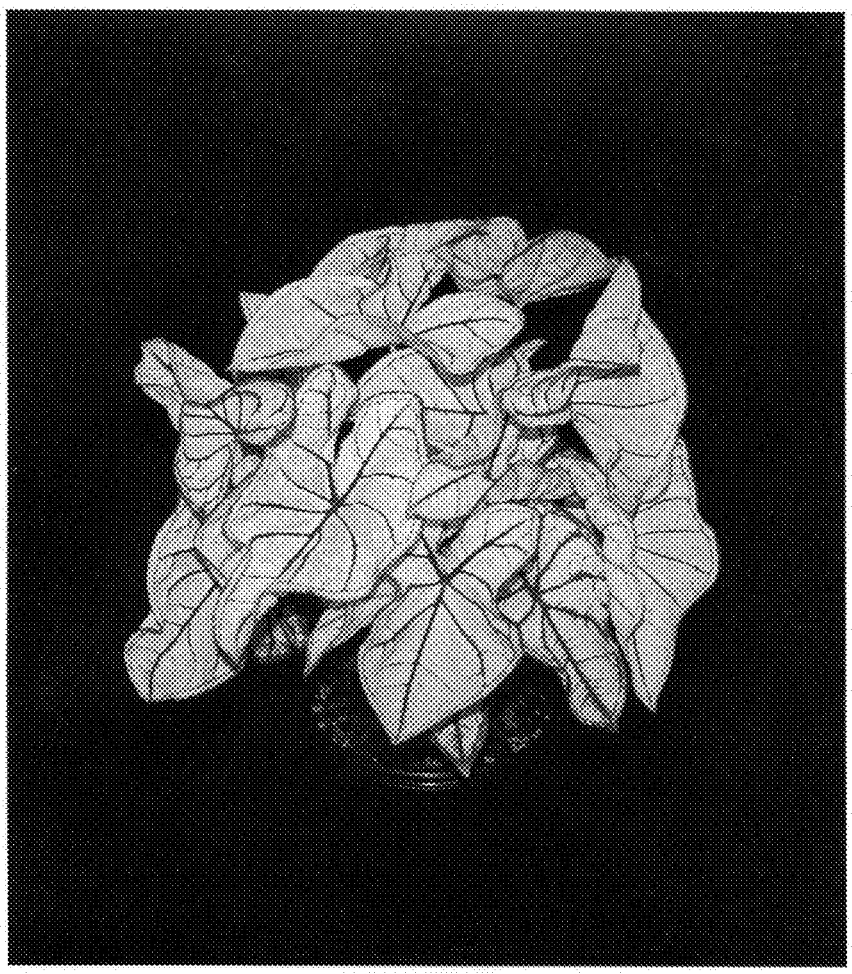

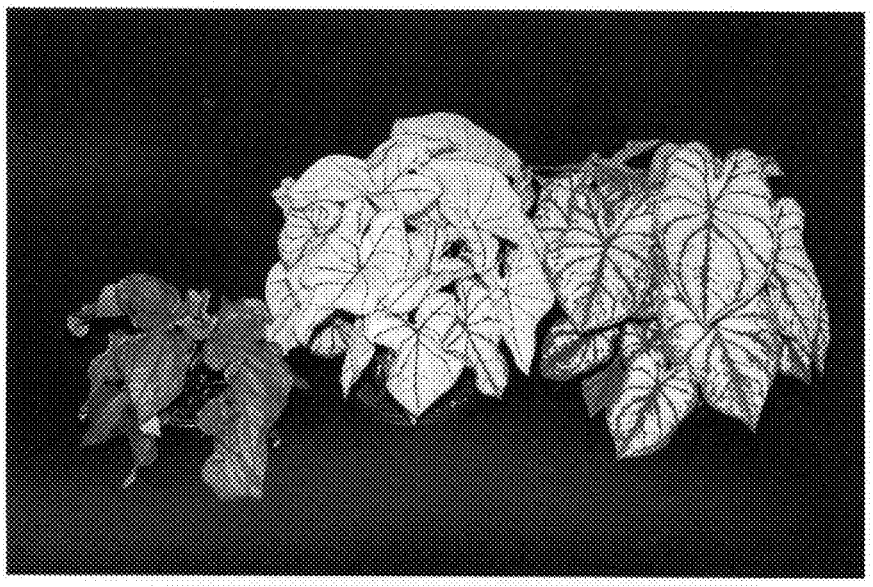
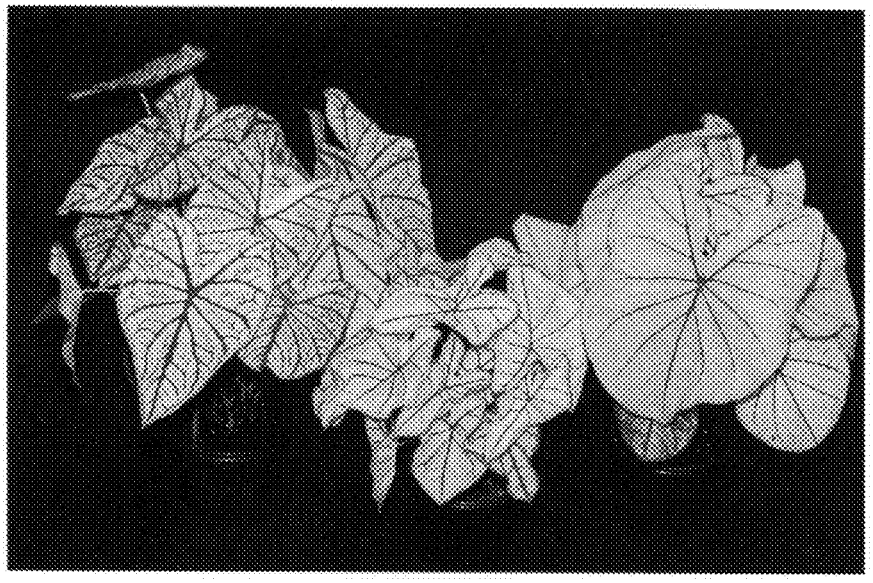

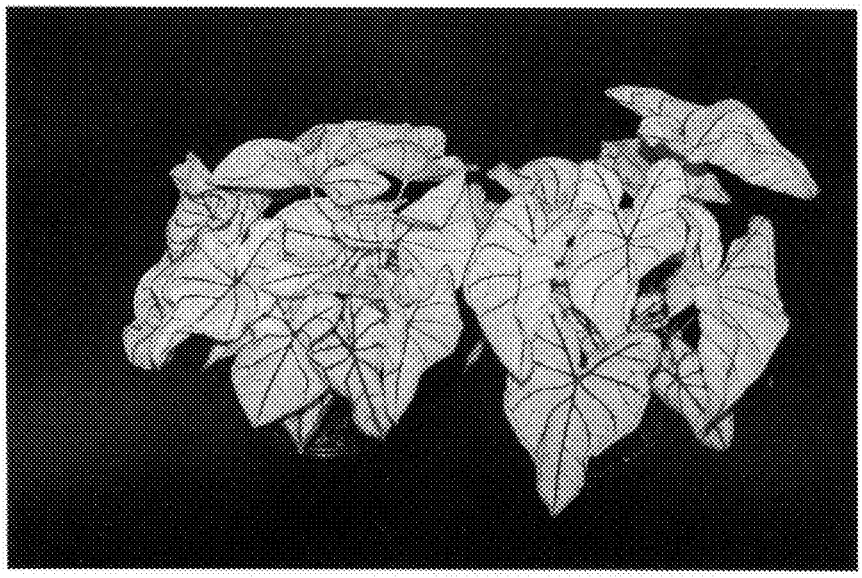
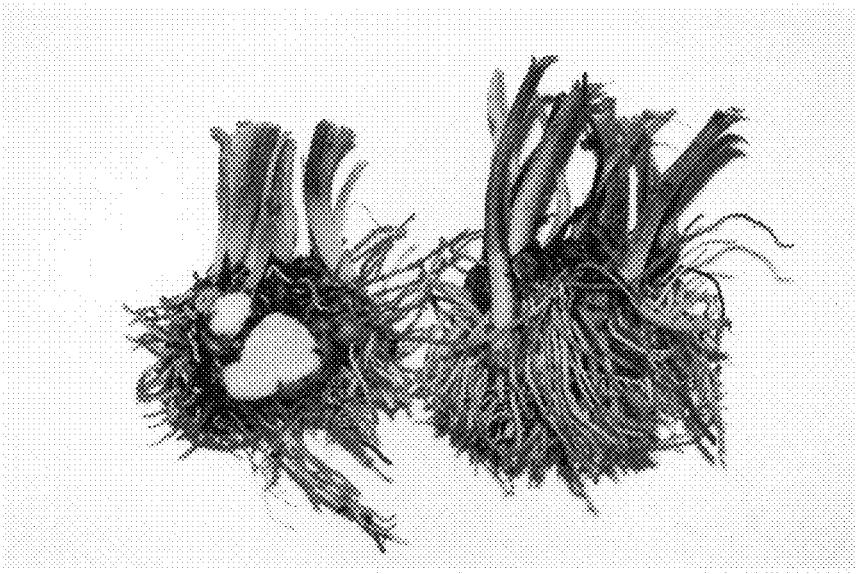

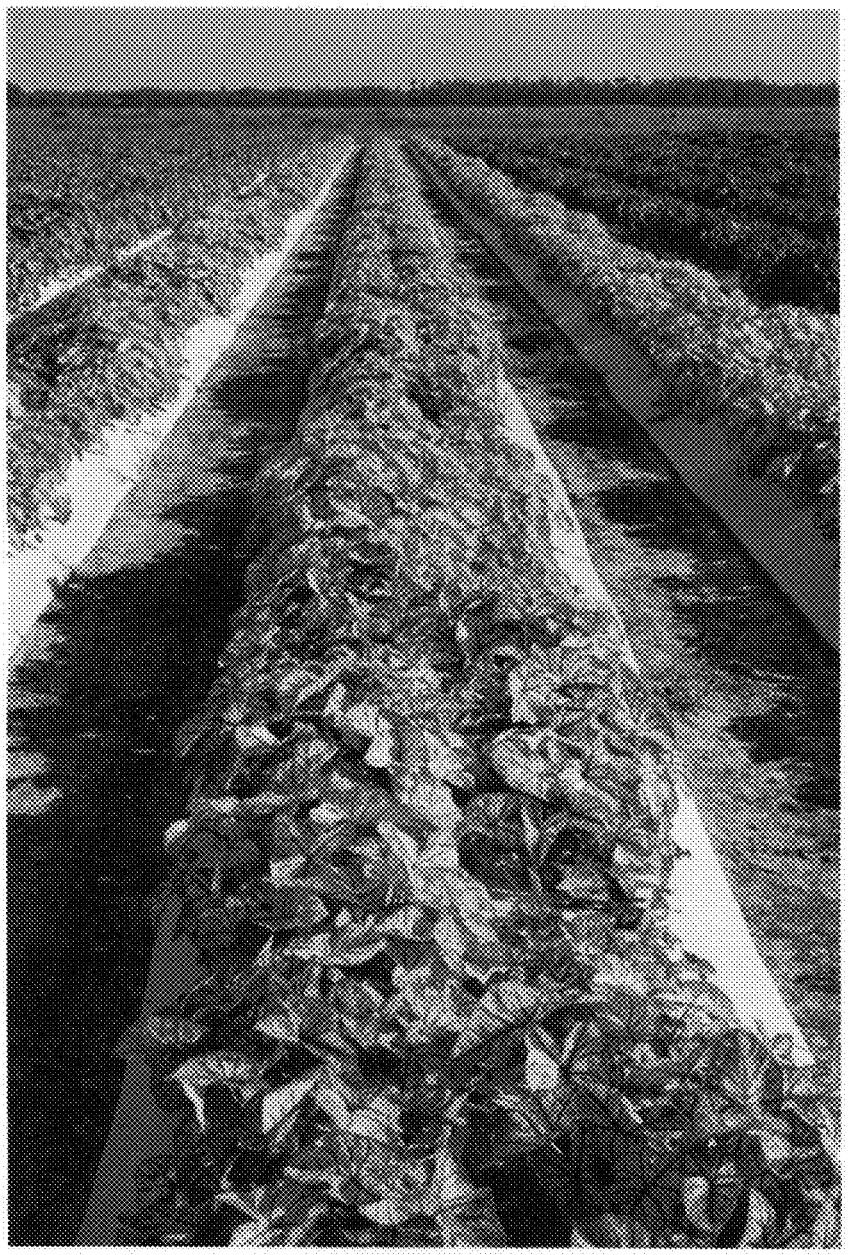

* * * * *